(12) United States Patent
Wolinsky et al.

(10) Patent No.: US 10,271,856 B2
(45) Date of Patent: Apr. 30, 2019

(54) VETEBRAL OSTEOTOMY SAW GUIDE

(71) Applicant: THE JOHNS HOPKINS UNIVERSITY, Baltimore, MD (US)

(72) Inventors: Jean-Paul Wolinsky, Baltimore, MD (US); Dan Stoianovici, Reisterstown, MD (US)

(73) Assignee: The Johns Hopkins University, Baltimore, MD (US)

( * ) Notice: Subject to any disclaimer, the term of this patent is extended or adjusted under 35 U.S.C. 154(b) by 265 days.

(21) Appl. No.: 15/267,300

(22) Filed: Sep. 16, 2016

(65) Prior Publication Data
US 2017/0079666 A1 Mar. 23, 2017

Related U.S. Application Data

(60) Provisional application No. 62/219,719, filed on Sep. 17, 2015.

(51) Int. Cl.
*A61B 17/15* (2006.01)
*A61B 17/14* (2006.01)

(52) U.S. Cl.
CPC ............ *A61B 17/15* (2013.01); *A61B 17/149* (2016.11)

(58) Field of Classification Search
CPC .. A61B 17/14; A61B 17/149; B66D 2700/028
See application file for complete search history.

(56) References Cited

U.S. PATENT DOCUMENTS 1,508,664 A * 9/1924 Mize .................. B66D 3/06
254/394

2008/0147084 A1 * 6/2008 Bleich ............ A61B 17/320016
606/114

OTHER PUBLICATIONS

Stener, B. "Total spondylectomy in chondrosarcoma arising from the seventh thoracic vertebra" J Bone Joint Surg. 1971; 53-B:288-295.
Roy-Camille et al. Total excision of thoracic vertebrae. Rev Chir Orthop Reparatrice Appar Mot. 1981; 67:421-430.
Gasbarrini, A., et al. "Influence of a thread wire saw guide and spinal cord protector device in "en bloc" vertebrectomies", J Spinal Disord Tech. Apr. 2012;25(2):E7-12.
Tomita, K., et al. "Surgical Strategy for Spinal Metastases" Spine 2001; 26: 298-306.

(Continued)

*Primary Examiner* — Andrew Yang
(74) *Attorney, Agent, or Firm* — Johns Hopkins Technology Ventures

(57) ABSTRACT

The Vertebral Osteotomy Saw Guide allows precise osteotomies to be performed through the vertebral column in conjunction with a thread-wire saw. The guide is designed so that it can mount to rods commonly used during spinal surgery for spinal stabilization. The mount of the guide is a polyaxial mount, allowing the angle of the guide mount to be adjusted and locked to create a desired cutting plane to produce a precise osteotomy. The guide itself consists of two interdigitated pulley wheels that allow the thread-wire saw to pass smoothly through the guide. The simple, but unique design of the guide allows a surgeon to perform an osteotomy through the vertebral column cutting from one side of the vertebral column to the other. This unique orientation allows the osteotomy to be performed away from critical structures in the region (the spinal cord, aorta, and inferior vena cava).

18 Claims, 4 Drawing Sheets

(56) References Cited

OTHER PUBLICATIONS

Kawahara, T., et al. "Total en bloc spondylectomy for spinal tumors: surgical techniques and related basic background" Orthop Clin N Am 2009; 40: 47-63.

Hseih, P., et al. "Posterior-only approach for total en bloc spondylectomy for malignant primary spinal neoplasms: anatomic considerations and operative nuances" Neurosurgery. Dec. 2009; 65(6 suppl): 173-81.

* cited by examiner

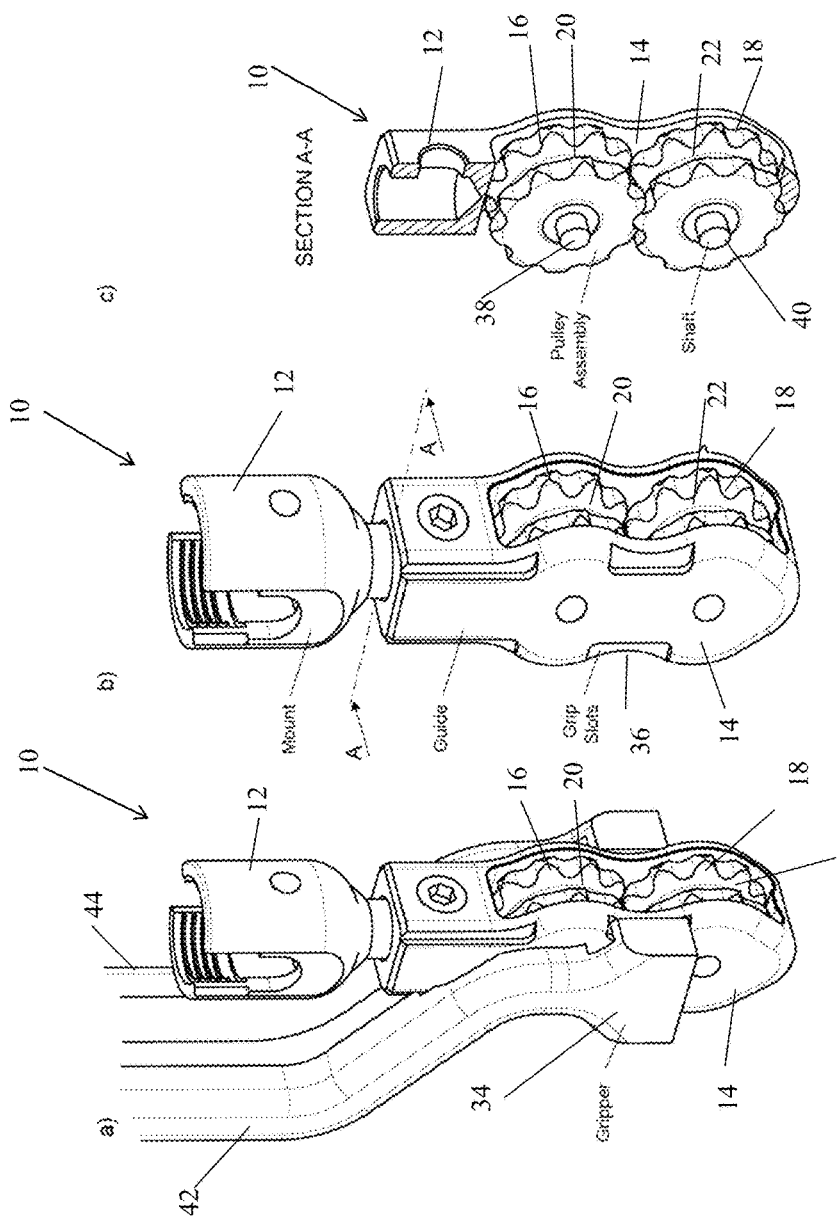

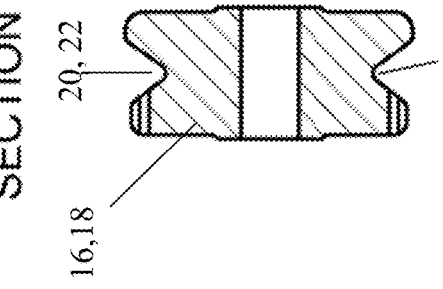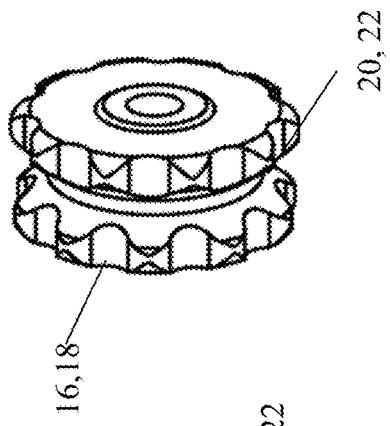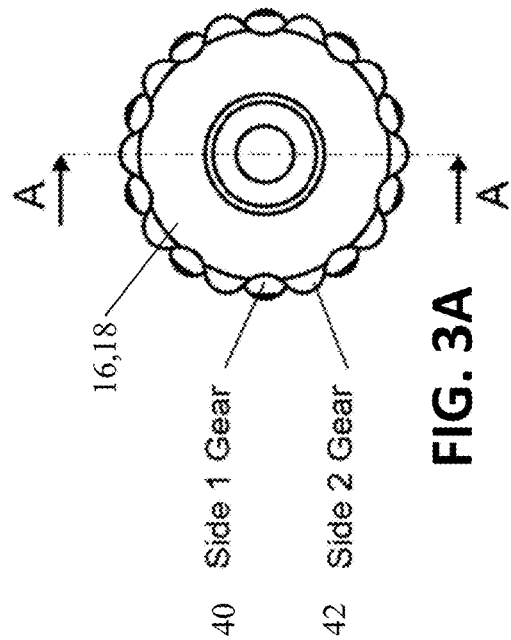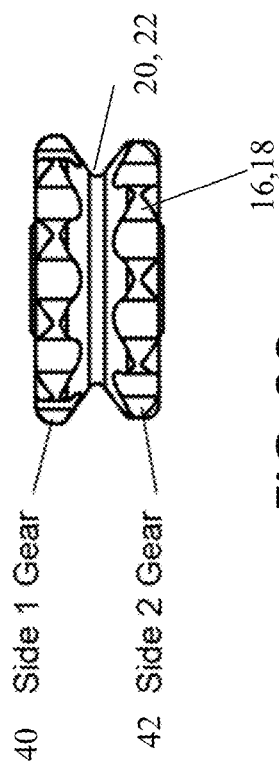

VETEBRAL OSTEOTOMY SAW GUIDE

CROSS REFERENCE TO RELATED APPLICATION

This application claims the benefit of U.S. Provisional Patent Application No. 62/219,719 filed on Sep. 17, 2015, which is incorporated by reference, herein, in its entirety.

FIELD OF THE INVENTION

The present invention relates generally to medical devices. More particularly, the present invention relates to a vertebral osteotomy saw guide.

BACKGROUND OF THE INVENTION

Osteotomies through a vertebral segment can be performed in many different ways. This can be achieved with osteotomes, drills, reciprocating saws, and wire saws. The standard surgical wire saws are gigli saws. These are wire saws with barbs along the wire, which cut when drawn across a surface. The barbs along the saws can unintentionally cut soft tissue structures that come into contact with the wire. These wire saws were modified by Tomita, and the thread-wire saw, or Tomita saw was developed. These saws are wire saws that have industrial diamonds attached to the wire, and cutting is achieved with these diamonds as they are drawn across a surface. This type of saw was initially developed for laminoplasty, as it was found to be gentle and safe when used in proximity to the dura surrounding the spinal cord. Although the saw comes into contact with soft tissue, the abrasive nature of the saw is too low to grab and cut such surfaces. These saws were later used by Tomita, and others, to perform osteotomies through vertebral bodies during en bloc resection of tumors.

En bloc resections of tumors in the spine, require multiple osteotomies to free the specimen from the spinal column. For example, if a tumor is situated ventrally, in the vertebral body, the vertebral body has to be separated (through osteotomies) from the posterior elements of the spine (pedicles, lamina, facet joints, spinous process) and the adjacent level of the spine (the vertebral segment just rostral and just caudal to the involved level). Mobilization of the tumor in this fashion allows the specimen to be delivered away from the spinal cord to prevent neurologic injury.

Sterner, Roy Camille, and later Tomita, developed an operation to achieve such resections in the thoracic spine. The operation is performed through an entirely posterior approach. The posterior elements of the spine are removed. The ventral vascular structures (the aorta and inferior vena cava) are mobilized away from the spinal surface. A ventral osteotomy is performed through the vertebral column, rostral and caudal to the margin of the tumor. Dr. Tomita's modification of this technique incorporates the use of a thread-wire saw for the osteotomies. A Tomita saw is placed around the ventral aspect of the spine. One is located rostral and one is located caudal to the margin of the tumor. A metal guard (retractor) is then placed between the dura and the spine to protect the spinal cord during the osteotomy, and is held manually in place. The osteotomy is performed with the Tomita saw, cutting the vertebral column from anterior to posterior, thus, the cutting action is towards the spinal cord, therefore the dura and spinal cord are placed at risk during this maneuver. A modification of this technique has been made by Boriani and Gasbarrini. A guard is placed between the dura and the spinal cord, and is mounted to the spinal instrumentation. The guard is fixed to the instrumentation so that when the thread-wire is used to cut the osteotomy from the ventral aspect of the vertebral column to the posterior aspect, the wire in theory will be prevented from being pulled into the spinal cord. Both Tomita's and Boriani's technique require placement of a guard (retractor) in the space between the spinal cord and the posterior aspect of the spinal column. As the osteotomy is performed from the ventral aspect of the spinal column to the posterior aspect of the spinal column, the spinal cord is placed at risk as the thread-wire is drawn towards it. The guard placed between the spinal cord and the posterior aspect of the vertebral column is placed to protect the cord. Failure of maintaining the guard in position, could result in spinal cord injury. In addition, the spinal cord is at significant risk during placement of the guard between the dura and the spinal column. This potential space is small, and insertion of a retractor or guard into this potential space adds mass, and places the spinal cord in potential risk.

Accordingly, it would be beneficial to provide a device for osteotomy to protect the spinal cord during procedures.

SUMMARY OF THE INVENTION

The foregoing needs are met, to a great extent, by the present invention which provides a device for osteotomy including a first pulley defining a channel. The channel is configured such that a threadwire can be disposed therein. The first pulley defines a first side and a second side disposed to either side of the channel. A second pulley defines a channel such that the threadwire can be disposed therein. The second pulley defines a first side and a second side disposed to either side of the channel, wherein the first pulley and the second pulley comprise a rolling action with respect to one another, such that the threadwire moves with a relative motion to an object predetermined to be cut. The device also includes a guide disposed on an outside surface of the first and second pulleys.

In accordance with an aspect of the present invention, the device includes an edge of the first side of the first pulley that defines a first gearing of the first side of the first pulley and an edge of the second side of the first pulley defines a second gearing of the second side of the first pulley. The second gearing of the second side of the first pulley is offset from the first gearing of the first side of the first pulley. The device also includes an edge of the first side of the second pulley that defines a first gearing of the first side of the second pulley and an edge of the second side of the second pulley defines a second gearing of the second side of the second pulley offset from the first gearing of the first side of the second pulley such that the first pulley and the second pulley are configured to move in tandem. The first and second gearing of the first pulley and the first and second gearing of the second pulley move in a direction of a movement of the threadwire. The first gearing of the first pulley is shifted angularly from the second gearing of the first pulley, such that the teeth of one are centered on the gap of the other, therefore doubling the number of effective teeth of the combined gear. The first gearing of the second pulley is shifted angularly from the second gearing of the second pulley, such that the teeth of one are centered on the gap of the other, therefore doubling the number of effective teeth of the combined gear.

In accordance with another aspect of the present invention, a mount is coupled to the guide such that the device can be secured in a surgical field. The device is configured to be positioned in an orientation in a plane and locked in the orientation in the plane for the osteotomy to be produced. The threadwire is passed ventral to the vertebral body and follows the contour of the vertebral body on a side of a spine contra-lateral to the guide. The device is configured to move the threadwire away from the aorta, spinal cord, and vena cava. The first pulley and the second pulley include a 1:1 gear connection. A smooth tooth profile for the first and second gearing of the first pulley and the first and second gearing of the second pulley can be used. The first and second pulleys include a tandem of two interlaced gears. The first and second pulleys include a standard gear configuration. The threadwire cuts the object predetermined to be cut and does not cut the device.

In accordance with yet another aspect of the present invention, a method for osteotomy includes reorienting a direction of a threadwire cutting action away from critical structures for safety, while applying the threadwire cutting action to an object predetermined to be cut.

In accordance with still another aspect of the present invention, the method includes using a device that cuts away from critical structures on a lateral side of the object predetermine to be cut. The method includes preventing the cutting action of the threadwire on the device for using the threadwire. The method also includes using a device with pulleys, wherein the pulleys are configured to roll in a direction of a movement of the threadwire. In addition, the method includes using geared pulleys. The method can also include providing an attachment of the device to a spinal instrumentation rod in place for the osteotomy.

BRIEF DESCRIPTION OF THE DRAWINGS

The accompanying drawings provide visual representations, which will be used to more fully describe the representative embodiments disclosed herein and can be used by those skilled in the art to better understand them and their inherent advantages. In these drawings, like reference numerals identify corresponding elements and:

FIGS. 2A-2C illustrate the VOS device, according to an embodiment of the present invention.

FIGS. 3A-3D illustrate the pulley and tandem gear geometry, according to an embodiment of the present invention.

DETAILED DESCRIPTION

Figure 1A:
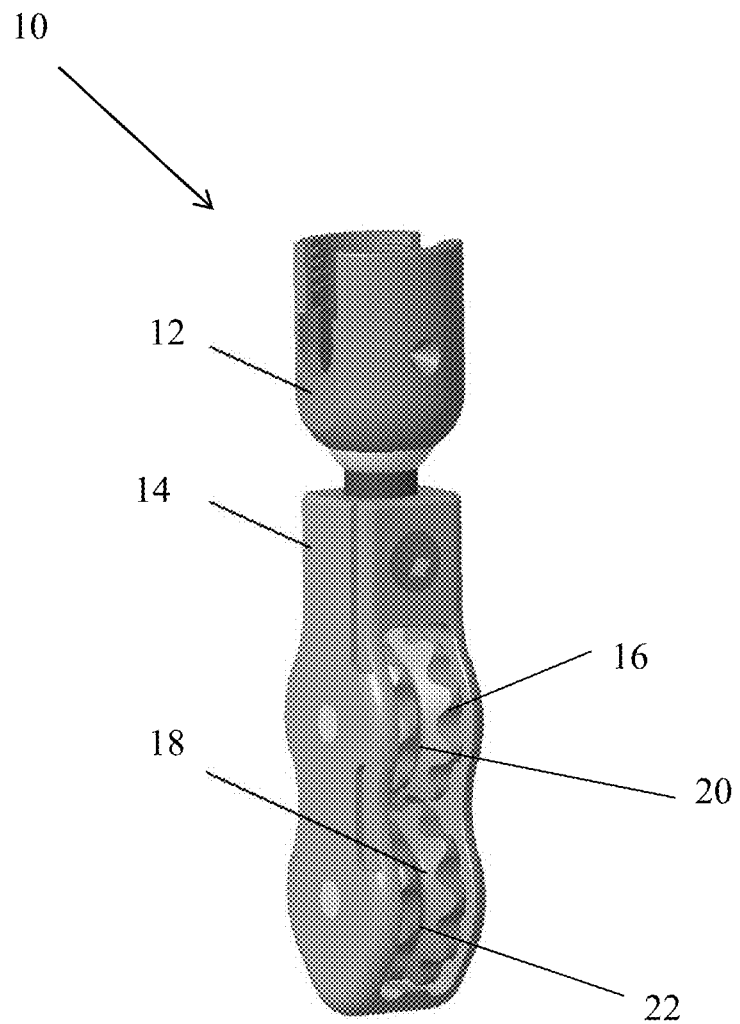
FIGS. 1A and 1B illustrate a guide and a mount, according to an embodiment of the present invention.

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

An embodiment in accordance with the present invention is directed to a vertebral osteotomy saw guide that allows precise osteotomies to be performed through the vertebral column in conjunction with a thread-wire saw. The guide is designed so that it can mount to rods commonly used during spinal surgery for spinal stabilization. The mount of the guide is a polyaxial mount, allowing the angle of the guide mount to be adjusted and locked to create a desired cutting plane to produce a precise osteotomy. The guide itself consists of two interdigitated pulley wheels that allow the thread-wire saw to pass smoothly through the guide. The simple, but unique design of the guide allows a surgeon to perform an osteotomy through the vertebral column cutting from one side of the vertebral column to the other. This unique orientation allows the osteotomy to be performed away from critical structures in the region (the spinal cord, aorta, and inferior vena cava). The intention of the guide is to produce a reliable, planned osteotomy, and decrease the potential morbidity and mortality of a major vascular or spinal cord injury. The interdigitation of the pulley wheels is designed to decrease friction between the wheel and the thread wire saw to decrease wear abrasion on the system.

In order to minimize risk to critical structures in the spinal region, the vertebral osteotomy saw guide of the present invention was developed. The guide is placed lateral to, and adjacent to the spine. It is held in position by mounting it to the spinal hardware. The coupler is designed so that the guide can be oriented and fixed in a position to create the desired cutting plane of the osteotomy. A threadwire saw is passed ventral to the vertebral body, and then follows the contour of the vertebral body on the side of the spine contra-lateral to the saw guide. The saw is then brought back across the posterior aspect of the vertebral body, ventral to the dura and spinal cord, to the saw guide. Each end of the guide is threaded around the pulley wheels of the saw guide. This unique configuration holds the saw in the desired orientation for the planar cut and allows the osteotomy to be performed from side to side. This results in the cut being performed in such a way that the aorta and inferior vena cava as well as the spinal cord and dura are placed at much lower risk for injury during the osteotomy. This is different than the technique proposed by Tomita and others, where the osteotomy is performed from ventral to posterior, cutting the spinal column in a direction towards the spinal cord. The wheels on the saw guide have been designed to gear into one another. This configuration allows the wheels to turn in tandem with each other. This feature decreases the chance of drag of the thread wire on the pulley wheel and therefore potentially decreases wear debris.

The features of the device allow the device to be oriented and locked in its orientation in the desired plane for the osteotomy to be produced. In addition, the device allows the osteotomy to be performed through an orientation that brings the saw away from critical structures (spinal cord, aorta, vena cava), thus decreasing the chance of devastating, mortal injuries.

Figure 1B:
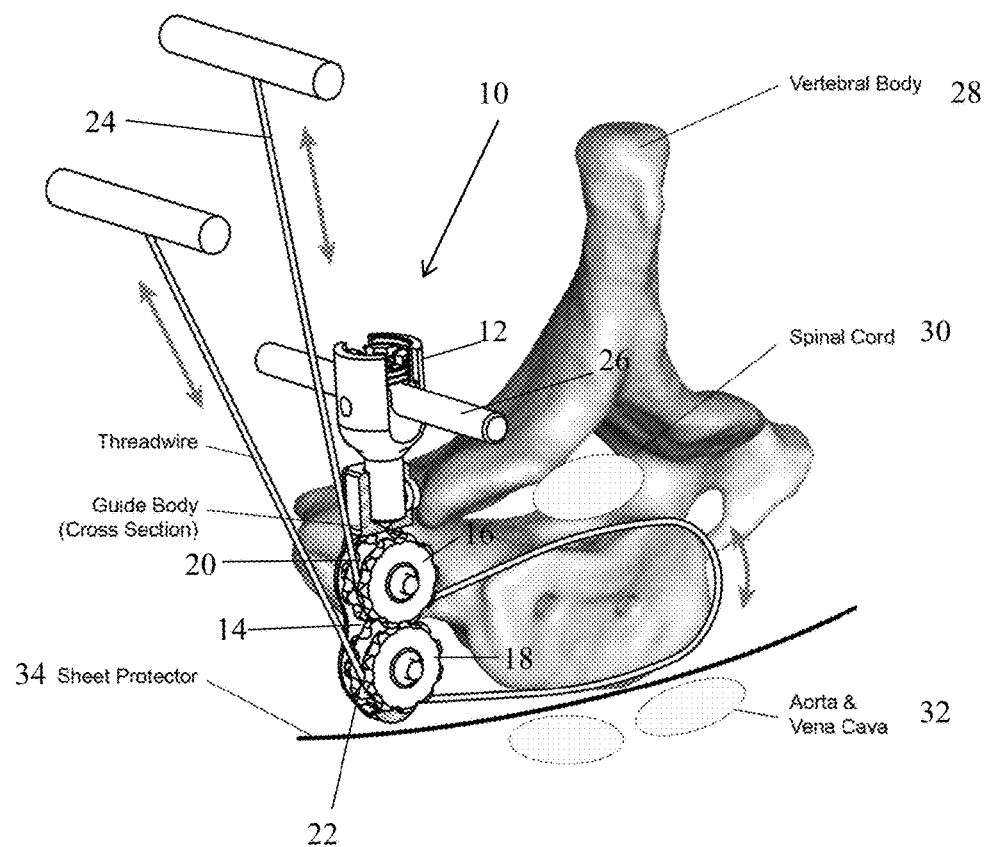

FIGS. 1A and 1B illustrate a guide and a mount, according to an embodiment of the present invention. The guide includes two pulley wheels, designed to allow the flow of the saw through the guide, without cutting into the guide, and a housing that holds the wheels. The mount allows the device to be mounted to the rods along the spinal instrumentation, or on a bed mounted retractor system, and orients the guide in the correct cutting plane. FIGS. 1A and 1B illustrate how the guide is mounted to the spinal instrumentation rod locked into position, and how the threadwire is guided around the vertebral body and through the device. The movement of the threadwire saw through the VOS guide is illustrated, and as can be seen, the direction of the osteotomy is guided away from the spinal cord, aorta and inferior vena cava. The pulleys can include gearing or can also work without gearing. The pulleys roll in the direction of movement of the threadwire. In this manner, the threadwire cuts the object predetermined to be cut, such as the vertebral bone and does not cut the device (i.e. the pulleys on which the threadwire rests). The relative motion of the threadwire with respect to the vertebral bone, or object predetermined to be cut, allows for that vertebral bone or object predetermined to be cut to be cut by the threadwire.

As illustrated in FIG. 1A the device 10 includes a mount 12 and a guide 14. Pulleys 16, 18 are disposed within the guide 14. The pulleys 16, 18 include grooves 20, 22 that facilitate movement of the threadwire (not pictured). FIG. 1B illustrates the device 10 in position for an osteotomy. As illustrated in FIG. 1B a threadwire 24 is disposed in grooves 20, 22 of the pulleys 16, 18 in order to facilitate the osteotomy procedure. FIG. 1B illustrates a partially sectional view of the device 10, such that only the back portion of the guide 14 is illustrated and the faces of pulleys 16, 18 are shown. The mount 12 is coupled to one of spinal instrumentation rods 26 associated with the procedure and positioned adjacent to the vertebral body 28. The device 10 of the present invention positions the threadwire 24 in such a way that the spinal cord 30 and the aorta and vena cava 32 are protected. An additional sheet protector 34 can be used to further protect the aorta and vena cava.

FIGS. 2A-2C illustrate the VOS device, according to an embodiment of the present invention. FIG. 2A illustrates a gripper 34 holding the device 10. FIG. 2B illustrates the device 10 including the mount 12, the guide 14, and gripper slots 36. FIG. 2C illustrates a central cross section through the guide showing pulley assemblies 16, 18 and shafts 38, 40 (section on the body of the guide only). A gripper 34 is used to handle the device to facilitate its placement and attachment to the rods (not pictured) as illustrated in FIG. 2A. The gripper extends two arms 42, 44 that grip on gripper slots 36 made on the sides of the guide (FIG. 2B). Conveniently, these were made so that the pliers used to handle standard pedicle screws can also be used to handle the VOS device. FIG. 2C illustrates a central cross section through the guide 14. FIG. 2C shows two pulley assemblies 16, 18 supported on to the body of the guide by shafts 38, 40. Because the threadwire is made of highly abrasive material, pulleys are used to facilitate the motion of the threadwire over its bends. Moreover, the outer parts of the pulleys are toothed so that the pulleys implement a 1:1 gear connection. This keeps the motion of both pulleys 16, 18 in sink to the motion of the threadwire in its reciprocating motion, as such.

Referring to FIG. 1B, when the surgeon pulls the top handle of the threadwire 24, this engages the top pulley 16 causing it to spin clockwise. Gearing then engages the bottom pulley 18 to spin counterclockwise. This corresponds to the direction that the bottom wire moves out of the device towards the bottom handle. On the other direction of the reciprocating motion, the threadwire 24 engages the bottom pulley 18, which causes the top pulley 16 to spin, so that it matches the way that the threadwire 24 at the top moves out of the device 10. Gearing the pulleys minimizes the slippage of the threadwire 24 relative to the pulleys, therefore reducing the wear of the pulleys 16, 18 by the threadwire 24.

While a standard gear could be used for gearing pulleys 16, 18, a custom tooth geometry is used for the present invention so that the teeth have smooth profiles and do not damage tissues. However, rounder gear geometry with larger teeth reduces the number of gear teeth. As such, a tandem of two interlaced gears were used to improve the kinematic engagement. Both pulleys used in the device are identical. The design of the pulleys is illustrated in FIGS. 3A-3D. FIGS. 3A-3D illustrate the pulley and tandem gear geometry, according to an embodiment of the present invention. The pulleys 16, 18 present a central channel 20, 22 through which the threadwire is passed and two gears on the sides, set in tandem. The figure shows how the gear on one side 40 is shifted angularly from the gear on the other side 42, so that the teeth of one are centered on the gap of the other, therefore doubling the number of effective teeth of the combined gear.

The many features and advantages of the invention are apparent from the detailed specification, and thus, it is intended by the appended claims to cover all such features and advantages of the invention, which fall within the true spirit and scope of the invention. Further, since numerous modifications and variations will readily occur to those skilled in the art, it is not desired to limit the invention to the exact construction and operation illustrated and described, and accordingly, all suitable modifications and equivalents may be resorted to, falling within the scope of the invention.

What is claimed is:

1. A device for osteotomy comprising:
a first pulley defining a channel configured such that a threadwire can be disposed therein and the first pulley defines a first side and a second side disposed to either side of the channel,
a second pulley defining a channel such that the threadwire can be disposed therein and the second pulley defines a first side and a second side disposed to either side of the channel, wherein the first pulley and the second pulley comprise a rolling action with respect to one another such that the threadwire moves with a relative motion to an object predetermined to be cut;
a guide disposed on an outside surface of the first and second pulleys; and
wherein the first pulley and the second pulley comprise a 1:1 gear connection.

2. A device for osteotomy comprising:
a first pulley defining a channel configured such that a threadwire can be disposed therein and the first pulley defines a first side and a second side disposed to either side of the channel,
a second pulley defining a channel such that the threadwire can be disposed therein and the second pulley defines a first side and a second side disposed to either side of the channel, wherein the first pulley and the second pulley comprise a rolling action with respect to one another such that the threadwire moves with a relative motion to an object predetermined to be cut;
a guide disposed on an outside surface of the first and second pulleys;
wherein an edge of the first side of the first pulley defines a first gearing of the first side of the first pulley and an edge of the second side of the first pulley defines a second gearing of the second side of the first pulley, wherein the second gearing of the second side of the first pulley is offset from the first gearing of the first side of the first pulley; and
wherein an edge of the first side of the second pulley defines a first gearing of the first side of the second pulley and an edge of the second side of the second pulley defines a second gearing of the second side of the second pulley offset from the first gearing of the first side of the second pulley such that the first pulley and the second pulley are configured to move in tandem.

3. The device of claim 2 wherein the first and second gearing of the first pulley and the first and second gearing of the second pulley move in a direction of a movement of the threadwire.

4. The device of claim 2 further comprising the first gearing of the first pulley being shifted angularly from the second gearing of the first pulley, such that the teeth of one are centered on the gap of the other, therefore doubling the number of effective teeth of the combined gear.

5. The device of claim 4 further comprising the first gearing of the second pulley being shifted angularly from the second gearing of the second pulley, such that the teeth of one are centered on the gap of the other, therefore doubling the number of effective teeth of the combined gear.

6. The device of claim 2 further comprising a mount coupled to the guide such that the device can be secured in a surgical field.

7. The device of claim 2 further comprising the device being configured to be positioned in an orientation in a plane and locked in the orientation in the plane for the osteotomy to be produced.

8. The device of claim 2 wherein the threadwire is passed ventral to the vertebral body and follows the contour of the vertebral body on a side of a spine contra-lateral to the guide.

9. The device of claim 2 further comprising the device being configured to move the threadwire away from the aorta, spinal cord, and vena cava.

10. The device of claim 2 wherein the first pulley and the second pulley comprise a 1:1 gear connection.

11. The device of claim 2 further comprising a smooth tooth profile for the first and second gearing of the first pulley and the first and second gearing of the second pulley.

12. The device of claim 2 wherein the first and second pulleys comprise a tandem of two interlaced gears.

13. The device of claim 2 wherein the first and second pulleys comprise a standard gear configuration.

14. The device of claim 2 wherein the device is configured such that the threadwire cuts the object predetermined to be cut and does not cut the device.

15. A method for osteotomy comprising:
reorienting a direction of a threadwire cutting action away from critical structures for safety, while applying the threadwire cutting action to an object predetermined to be cut;
using a device that cuts away from critical structures on a lateral side of the object predetermine to be cut and
using a device with pulleys, wherein the pulleys are configured to roll in a direction of a movement of the threadwire.

16. The method of claim 15 further comprising preventing the cutting action of the threadwire on the device for using the threadwire.

17. The method of claim 15 further comprising using geared pulleys.

18. The method of claim 15 further comprising providing an attachment of the device to a spinal instrumentation rod in place for the osteotomy.

* * * * *